United States Patent
Van De Sluis et al.

(10) Patent No.: US 8,339,274 B2
(45) Date of Patent: Dec. 25, 2012

(54) SYSTEM AND METHOD FOR AUTOMATICALLY ADJUSTING A LIGHTING ATMOSPHERE BASED ON PRESENCE DETECTION

(75) Inventors: Bartel Marinus Van De Sluis, Eindhoven (NL); Jan Alexis Daniel Nesvadba, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 237 days.

(21) Appl. No.: 12/812,039

(22) PCT Filed: Jan. 13, 2009

(86) PCT No.: PCT/IB2009/050117
§ 371 (c)(1),
(2), (4) Date: Jul. 8, 2010

(87) PCT Pub. No.: WO2009/090598
PCT Pub. Date: Jul. 23, 2009

(65) Prior Publication Data
US 2010/0277333 A1     Nov. 4, 2010

(30) Foreign Application Priority Data
Jan. 16, 2008 (EP) .................................. 08100562

(51) Int. Cl.
*G08B 21/00* (2006.01)
(52) U.S. Cl. ............. 340/686.1; 340/541; 340/5.12
(58) Field of Classification Search ........... 340/686.1, 340/552, 573.1, 686.6, 541, 5.12, 5.3, 5.32, 340/5.7
See application file for complete search history.

(56) References Cited

U.S. PATENT DOCUMENTS
4,225,808 A    9/1980   Saraceni
(Continued)

FOREIGN PATENT DOCUMENTS
DE     102006024512 A1    11/2007
(Continued)

OTHER PUBLICATIONS
Eng et al: "ADA-Intelligent Space: An Artificial Creature for the Swiss Expo.002"; Proceedings of the 2003 IEEE International Conference on Robotics & Automation, Sep. 2003, pp. 4154-4159.
(Continued)

*Primary Examiner* — Daniel Previl
(74) *Attorney, Agent, or Firm* — Mark L. Beloborodov; John F. Salazar

(57) ABSTRACT

The invention relates to a feeding device (1) for introducing a piece of linen (12) to be ironed into an ironing unit by means of suction, the feeding device (1) being provided with a suction shaft (3) into which the piece of linen (12) can be sucked and a top suction portion (4) which is provided for sucking the piece of linen (12) into the suction shaft (3). The feeding device (1) comprises a blocking clamp (6) which is provided to secure the piece of linen (12) in a clamping position, and which is arranged in the feeding device (1) in such a way that there is located after the clamping of the piece of linen (12) a portion of this piece of linen (12) above this blocking clamp (6) that can be sucked by the top suction portion (4) into the suction shaft (3). The invention further relates to an ironing device, comprising an ironing unit for ironing a piece of linen (12) and a feeding unit (1) for feeding the piece of linen (12) to be ironed into the ironing unit.

7 Claims, 2 Drawing Sheets

U.S. PATENT DOCUMENTS

| | | | |
|---|---|---|---|
| 5,866,887 A * | 2/1999 | Hashimoto et al. | 235/98 R |
| 6,507,278 B1 * | 1/2003 | Brunetti et al. | 340/541 |
| 6,548,967 B1 | 4/2003 | Dowling et al. | |
| 2005/0237733 A1 * | 10/2005 | Laski et al. | 362/147 |
| 2005/0275626 A1 | 12/2005 | Mueller et al. | |
| 2006/0071605 A1 | 4/2006 | Diederiks | |
| 2006/0164240 A1 * | 7/2006 | Patchell | 340/552 |
| 2008/0172781 A1 * | 7/2008 | Popowich et al. | 4/476 |

FOREIGN PATENT DOCUMENTS

| | | |
|---|---|---|
| JP | 09129377 A | 5/1997 |
| JP | 2004335431 A | 11/2004 |
| JP | 2006270865 A | 10/2006 |
| JP | 2007005261 A | 1/2007 |
| WO | 2006038169 A1 | 4/2006 |
| WO | WO 2006/038169 * | 4/2006 |

OTHER PUBLICATIONS

Experiencelab—Testing the Technologies of Tomorrow; Philips Research Password, No. 29, Feb. 2007, pp. 6-11.

* cited by examiner

SYSTEM AND METHOD FOR AUTOMATICALLY ADJUSTING A LIGHTING ATMOSPHERE BASED ON PRESENCE DETECTION

FIELD OF THE INVENTION

The invention relates to the automatic adjusting a lighting atmosphere based on presence detection, particularly based on the detection of the presence of people in a monitored area.

BACKGROUND OF THE INVENTION

Advanced lighting systems are often able to create lighting atmospheres depending on a plurality of input parameters such as user interactions. Interactive lighting atmospheres can be stimulating and exciting for retail or hospitality environments since interactivity and dynamics can make the area more attractive and interesting, for example in a shop, in which certain locations may be highlighted depending on the presence of people in order to attract shoppers. More often advanced lighting systems are also equipped with several sensors, e.g. in each luminary, typically measuring environmental light conditions and human presence. This is happening because these types of sensors will become very cheap, and people will expect a certain level of interactivity and intelligence from advanced lighting systems. For instance, people will expect the lighting to switch off automatically if a room is no longer occupied, especially nowadays were energy saving is realized as common sense.

SUMMARY OF THE INVENTION

It is an object of the present invention to provide a novel system and method, which allow to automatically influencing a lighting atmosphere in an environment.

The object is solved by the independent claims. Further embodiments are shown by the dependent claims.

A basic idea of the invention is to adjust a lighting atmosphere based on presence detection in that the level of dynamics, particularly including interactivity, of a lighting atmosphere is made dependent on the level of the presence of people in a particular area. Particularly, the invention is based on user studies, which have shown that the use of interactivity and dynamics becomes less desired when more people are present in an area. The level of the presence of people in a particular area particularly means the crowdedness in the particular area.

An embodiment of the invention provides a system for automatically adjusting a lighting atmosphere based on presence detection, comprising
- at least one sensor for gathering information on the presence of people in a supervised area,
- a processing unit being adapted for determining the presence level of people on the supervised area based on the gathered information and for adjusting the lighting atmosphere based on the determined presence level by controlling the dynamics level of the lighting atmosphere depending on the determined presence level.

This allows for example to reduce the level of dynamics of the lighting atmosphere if the number of people in the supervised area increases, i.e. the supervised area becomes crowded. Thus, a lighting atmosphere, particularly the dynamics of a lighting atmosphere may be automatically influenced in an environment such as s shop.

According to a further embodiment of the invention, the at least one sensor may comprise one or more of the following: a grid of infra-red presence sensors; a floor embedded presence sensor; a computer vision camera.

This implementations of the at least one sensor allow to reliably detect the crowdedness in the supervised area.

The processing unit may be further adapted in an embodiment of the invention to receive the gathered information from the at least one sensor by wired or wireless communication means. For example, the at least one sensor may comprise a powerline communication module, a network interface, a radio interface such as a ZigBee™ communication module or an optical communication module such as an infrared communication module.

According to a further embodiment of the invention, the processing unit may be adapted for determining the presence level of people by determining one or more of the following: determining the number of people being located in the supervised area; determining the number of people passing the supervised area within a predetermined period. For example, the processing unit may be adapted to count people in the supervised area and to determine the changes of the number of counted people over certain periods in order to determine the presence level. The number of the people corresponds to the crowdedness in the area, whiled the changes of the number or the people corresponds to the changes of crowdedness.

The processing unit may be in a further embodiment of the invention adapted to compare the determined presence level with a threshold and to adjust the lighting atmosphere, if the determined presence level is above the threshold. This allows to adjust the dynamics contained in the lighting atmosphere when the threshold is exceed, i.e. the presence of people in the supervised area is too high compared to the presence level predetermined by the threshold.

The threshold may be manually adjusted in an embodiment of the invention, thus allowing users to adapt the threshold to for example situations, in which the automatic behavior of the system as determined by a fixed or predefined threshold would generate dissatisfying results. The system may for example comprise a user interface with a dial knob or button for adjusting the threshold.

In a further embodiment of the invention, the processing unit may be adapted to automatically adjust the threshold in accordance with a schedule. This allows for example scheduling various thresholds throughout a day or week. For instance, retailers may know that at certain times there is a specific type of visitors in the area, e.g. older shoppers during the morning, and younger ones in the afternoon, for which a specific threshold could be applied. The schedule may be for example input by a user interface of the system or via a control interface for example with a lighting system, which comprises a computer controlled user interface, which may offer a user to input a schedule for various thresholds and their time of activation during a day, week, month, year etcetera. Thus, a lighting atmosphere, particularly the dynamics of a lighting atmosphere may be better adapted to an environment such as s shop.

According to a further embodiment of the invention, the processing unit may be adapted to control the dynamics level of the lighting atmosphere in that prominent dynamic effects of the lighting atmosphere are either disabled or adjusted to be less dynamic, if the determined presence level is above the threshold. For example, blinking lights may be switched off, or dynamic light effects such as changing colors may be disabled in a lighting atmosphere.

The processing unit may be further adapted in an embodiment of the invention for adjusting the lighting atmosphere based on the determined presence level by controlling the dynamics level of the lighting atmosphere directly depending on the determined presence level, wherein the level of dynamics is lowered if the determined presence level raises. In contrast to the detection of exceeding a threshold, this embodiment allows to more smoothly change the dynamics level of the lighting atmosphere.

In a further embodiment of the invention, the processing unit may be adapted for setting the level of dynamics to the lowest level, if the determined presence level is above a threshold. This may further enhance the smoothly changing of the dynamics level of a lighting atmosphere by disabling dynamic light effects of the lighting atmosphere when the detected presence in the supervised area is too high.

The system may be in further embodiment of the invention implemented as part of a lighting controller of a lighting system or as standalone unit, which may comprise interfaces for coupling with a lighting system.

The invention provides in a further embodiment an atmosphere creation system comprising
- a lighting system comprising at least one light unit and being adapted to automatically generate a lighting atmosphere with the at least one light unit, and
- a system for automatically adjusting the generated lighting atmosphere based on presence detection according to the invention and as described above by controlling the lighting system.

The system for automatically adjusting the generated lighting atmosphere based on presence detection according to the invention may for example comprise a control interface for coupling with a lighting system, over which control signals for adjusting the dynamics in the lighting atmosphere are transmitted.

Furthermore, an embodiment of the invention provides a method for automatically adjusting a lighting atmosphere based on presence detection, comprising
- gathering information on the presence of people in a supervised area,
- determining the presence level of people on the supervised area based on the gathered information, and
- adjusting the lighting atmosphere based on the determined presence level by controlling the dynamics level of the lighting atmosphere depending on the determined presence level.

This method may be implemented as an algorithm, which may be for example executed by an embedded light system controller. The algorithm may be also integrated in a light unit, which comprises a presence sensor, thus, obtaining an autonomous device which allows to create a lighting atmosphere and to adapt the created lighting atmosphere to the crowdedness in an area supervised by the presence sensor of the light unit. This light unit creates a kind of smart lighting, suitable to be applied to complex lighting systems as applied for example in large shops, bars, hotels, museums etc.

According to a further embodiment of the invention, a computer program may be provided, which is enabled to carry out the above method according to the invention when executed by a computer. Thus, the method according to the invention may be applied for example to existing lighting systems, which may be extended with novel functionality and are adapted to execute computer programs, provided for example over a download connection or via a record carrier.

According to a further embodiment of the invention, a record carrier storing a computer program according to the invention may be provided, for example a CD-ROM, a DVD, a memory card, a diskette, or a similar data carrier suitable to store the computer program for electronic access.

Finally, an embodiment of the invention provides a computer programmed to perform a method according to the invention and comprising an interface for communication with a lighting system for adjusting a lighting atmosphere generated by the lighting system. The computer may be for example a Personal Computer (PC) adapted to control a lighting system, particularly for automatically create a user desired lighting atmosphere for example from an abstract description of the lighting atmosphere in XML, to generate control signals in accordance with the automatically created lighting atmosphere and to transmit the control signals over the interface to the lighting system.

BRIEF DESCRIPTION OF THE DRAWINGS

These and other aspects of the invention will be apparent from and elucidated with reference to the embodiments described hereinafter.

The invention will be described in more detail hereinafter with reference to exemplary embodiments. However, the invention is not limited to these exemplary embodiments.

DETAILED DESCRIPTION OF EMBODIMENTS

Figure 1:
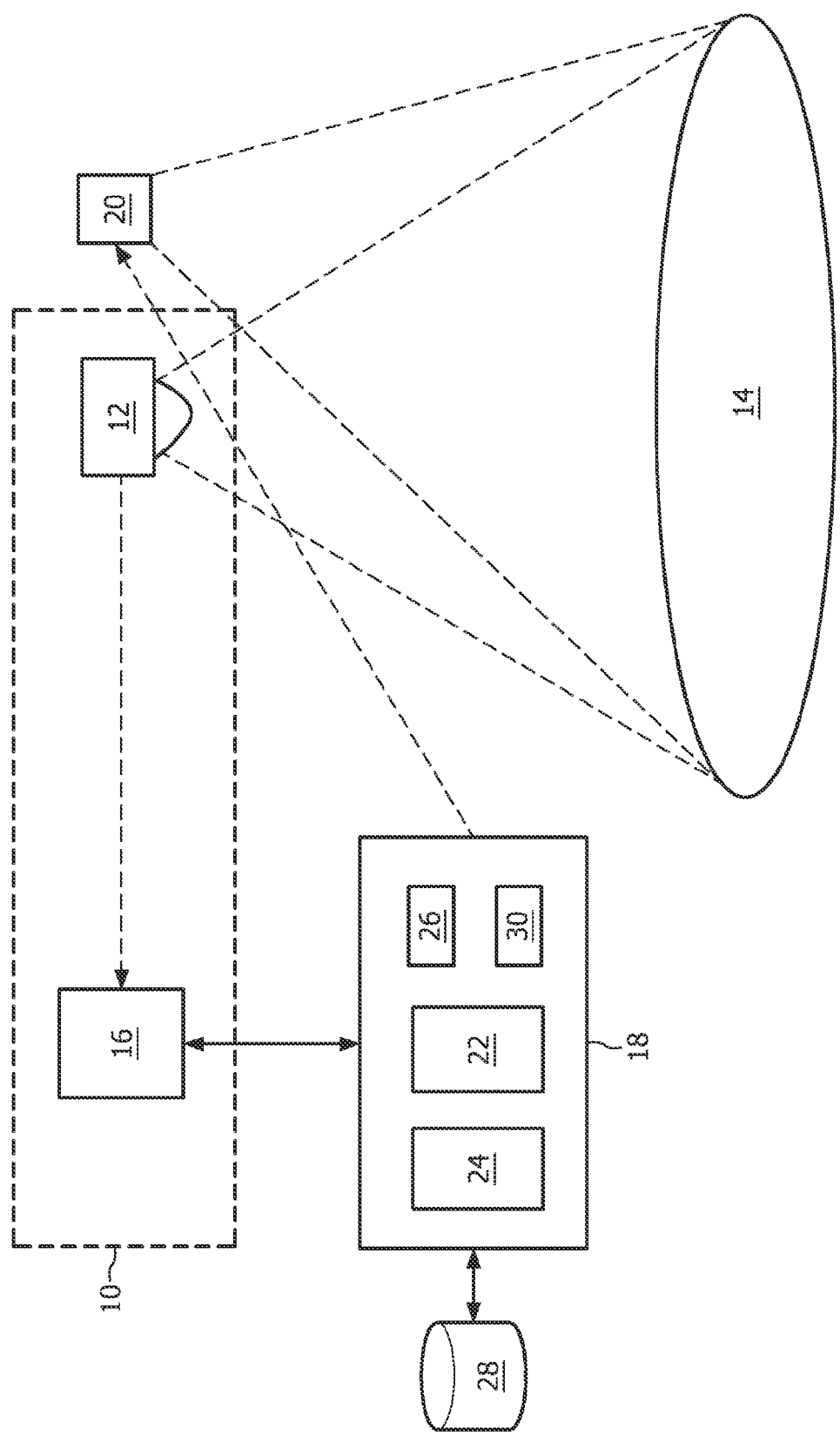
FIG. 1 shows an embodiment of a lighting system comprising a system for automatically adjusting a lighting atmosphere based on presence detection according to the invention.

In the following, functionally similar or identical elements may have the same reference numerals.

Interactive lighting atmospheres can be stimulating and exciting for people who are visiting a retail or hospitality environment such as a shop, boutique, hotel lobby or waiting area. Especially when these areas are relatively quiet the dynamics contained in interactive lighting atmospheres can make the area more attractive and interesting. Interactivity with regard to lighting comprises for example adapting a lighting to the presence of people, for example to change a certain light effect if people are approaching a specific area in a shop. Thus, interactivity comprises a dynamic lighting in the sense that the dynamics may be influenced by events, which are not controlled by a lighting system such as user behavior.

The inventors have been experimenting with various interactive lighting concepts which were evaluated with both retailers and shoppers. One example of these experiments is a reactive spotlight which illuminates a fashion accessory and creates a subtle change of light effect once a shopper approaches the fashion product. Retailers and shoppers appreciated this interactivity since it helps to turn shopping into an exciting journey of discovery. Many respondents remarked, however, that in quiet moments during the day the effect could even be more intense, and that at busy moments during the day, the effect should be subtle not to create a too dynamic environment. At moments that a shop is crowded, like in the weekends, the interactive effect may be undesired since shoppers are already confronted with an overload of stimulations and interactive lighting would add to the impression of "busyness" and create a negative effect. This experience caused the inventors to rethink the interactive lighting concepts, developed by them, and to propose to make the dynamics level of an atmosphere created by an atmosphere creation system such as a lighting system dependent on the level of human presence in a particular area.

FIG. 1 shows a lighting system comprising a lighting controller 18 and a spotlight 20. The lighting controller 18 is able to automatically generate control signals, which are transmitted wireless to the spotlight 20 to create a certain lighting atmosphere containing dynamics. The lighting controller 18 contains a processing unit 22 for processing a received lighting atmosphere and to generate control signals for the spotlight 20 to generate the light effects in accordance with the received lighting atmosphere, a lighting atmosphere receiving unit 24 for receiving a lighting atmosphere for example from a database 28, a wireless communication unit 26 for transmitting the generated control signals to the spotlight 20, and a presence sensor 30 for detecting people approaching an area 14, highlighted with the spotlight 20. In the area 14, new products in a shop may be for example presented.

The lighting atmosphere receiving unit 24 receives lighting atmosphere data in the form of a file containing an abstract description of a lighting atmosphere from the database 28 and forwards the received data to the processing unit 22. The processing unit 22 automatically generates from the received data control signals suitable to generate the light effects in accordance with the received lighting atmosphere with the light units contained in the concrete lighting system, here with the spotlight 20. The generated control signals are then transmitted wireless via the wireless communication unit 26 from the lighting controller 18 to the spotlight 20, which generates the desired light effects. The lighting controller 18 implements together with the controlled spotlight 20 an interactive lighting atmosphere, i.e. a dynamic lighting atmosphere which "reacts" on environmental changes as will be described next. When people approach the area 14, the presence sensor 30 of the lighting controller detects and signals this event to the processing unit 22. The processing unit 22 then generates control signals for the spotlight in order to create changing light effects, which may attract the people to the area 14.

Furthermore, a system 10 for automatically adjusting the lighting atmosphere based on presence detection is provided, which may automatically influence the created lighting atmosphere depending on the presence level in the area 14 as will be described in the following. The system 10 comprises a presence sensor 12, which is configured to supervise the area 14, which is highlighted by the spotlight 20. The presence sensor 12 gathers information on the presence of people in the supervised area 14 and forwards respective signals to a processing unit 16 of the system 10, which processes the received signals in the following way. The processing unit 16 determines from the received presence sensor signals the number of people located in the supervised area 14 and the number of the people passing the supervised area 14, i.e. entering or leaving the supervised area 14. The determined number of people corresponds to the presence level in the supervised area 14. The processing unit 14 further compares continuously the determined presence level with a threshold. The threshold is a predetermined presence level, which corresponds to a certain number of people located in and/or passing the supervised area 14. Typically, the predetermined presence level corresponds to a number of people at a busy time and which requires reducing dynamics in a lighting atmosphere, since these dynamics are considered by the people as undesired since the people are already confronted with an overload of stimulations and interactive lighting could create a negative effect to the attraction of people. Therefore, the processing unit 14 signals to the lighting controller 18 to adapt the lighting atmosphere and light effects created by the spotlight 20 in that dynamics of the lighting atmosphere are reduced, if the determined presence level is above the threshold. Upon receipt of this signaling from the processing unit 16 of the system 10, the processing unit 22 of the lighting controller 18 begins to adapt the lighting atmosphere by reducing the dynamics and also the interactivity, for example disables the light effects depending on the presence detection of the presence sensor 30. The disabling may be abrupt, for example by switching dynamic light effects off, or smooth, for example by dimming certain dynamic light effects.

Figure 2:
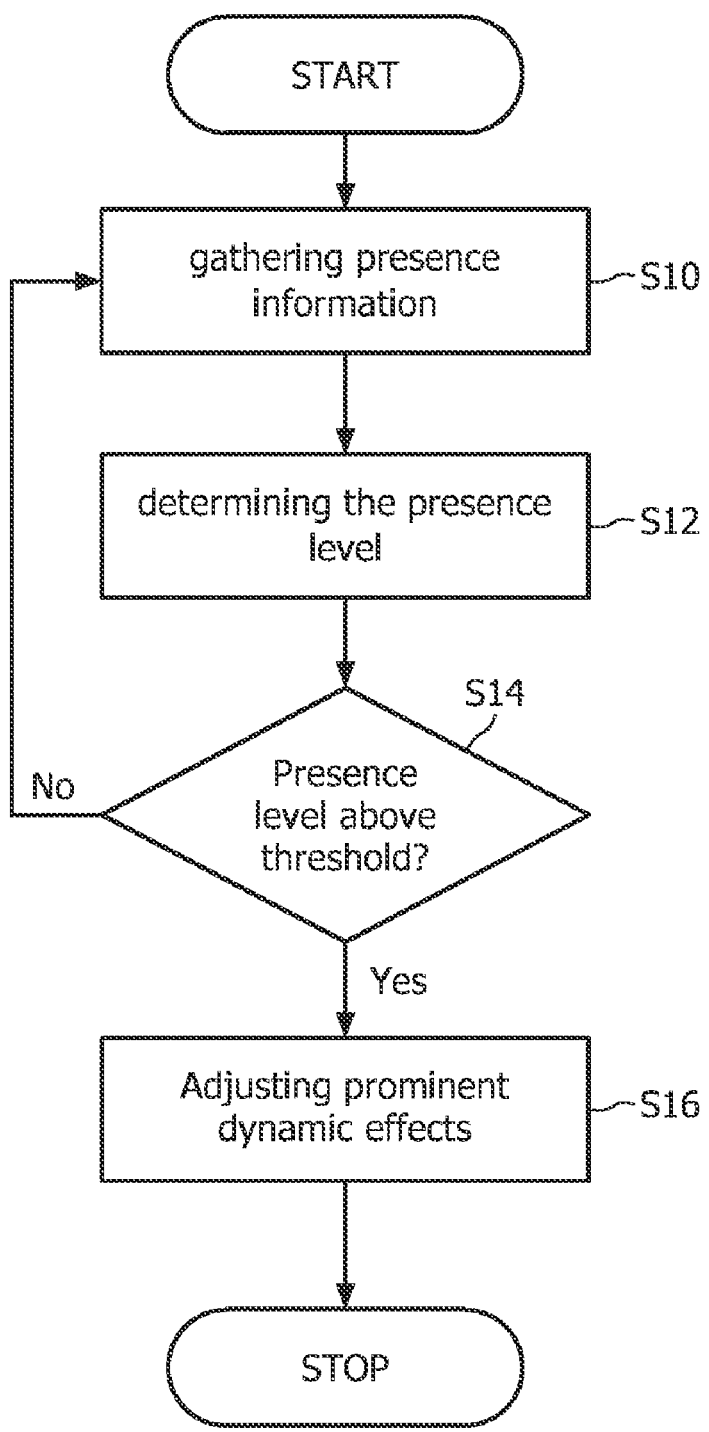
FIG. 2 shows an embodiment of a method for automatically adjusting a lighting atmosphere based on presence detection according to the invention.

FIG. 2 shows a flowchart of an algorithm embodying a method for automatically adjusting a lighting atmosphere based on presence detection. In a first step S10 of the algorithm, presence information from a supervised area is gathered, particularly with one or more presence sensors or detectors. On the basis of the gathered presence information, the presence level in the supervised area is determined in a following step S12. In a further step S14, it is checked whether the determined presence level is above a threshold, predefined for a specific presence in the supervised area as being to overcrowded for interactive lighting effects. If the determined presence level is below the threshold, the algorithm returns to step 10, in which further presence information is gathered. However, is the determined presence level is above the threshold, the algorithm continues with step S16, in which prominent dynamic effects of the lighting atmosphere are adjusted, particularly disabled or adjusted to be less dynamic.

It should be noted that the automatic creation of a lighting atmosphere with the lighting controller 18 is a complex process, during which an abstract description of a lighting atmosphere, which is not linked to a concrete embodiment of a lighting system, is mapped to the concrete lighting system controlled by the lighting controller 18. This process comprises particularly mapping light effects in semantic areas, as described in the abstract description, into light effects to be created with light units, provided in areas corresponding to the respective semantic areas, for example a certain light effect in the semantic area "cash register" is mapped into a corresponding light effect to be created by one or more light units provided in the cash register area of the target lighting system.

Possible additions and extensions of the invention are briefly explained in the following:
1. The invention can be provided and enhanced with methods to identify areas, i.e. semantic areas or islands, of crowdedness in a public or commercial space, e.g. department stores, fashion shops, soccer stadium.
2. The invention can be as well enhanced with anticipative attributes, i.e. the prediction of (semantic) areas, which will exhibit the attribute of crowdedness in the next moment. This can be achieved by sensor information, e.g. knowledge of moving patterns including speed and direction of individuals, which can be extrapolated and, hence, predict future areas of crowdedness. The knowledge of behavior patterns of specific target groups, e.g. leisure shoppers, can be used to enhance the reliability of the system and method according to the invention and as described above.
3. Behavior patterns of target or specific groups can be collected, e.g. using RFID (Radio Frequency Identification) or vision systems, and used to elaborate statistical behavior patterns for different day times, specific days, or even over periods over the year, e.g. summer, autumn, winter and spring. Hence, the lighting atmosphere or ambience, respectively, can be adapted accordingly for the specific target groups leading to some kind of personalization.
4. The knowledge of crowdedness in adjacent semantic area can be used to provide smooth ambience transitions between crowded and non-crowded areas. For example, the semantic area 'Women's Section' in the back of a shop is almost empty, but semantic area 'Special Offers' in the centre of the shop is crowded, still the transition should be smooth between the two ambiences.
5. Furthermore, the knowledge of behavior patterns as described under point 3 above and the knowledge of crowdedness in adjacent semantic areas can be used to timely trigger and adapt dynamic lighting effects and atmospheres anticipating the crowdedness status of the semantic area in the close future. For example, knowing that the 'Special Offer' section is crowded and that based on behavior patterns the crowd usually moves to 'Women's section', the long-lasting dynamic lighting effect in the 'Women's section' can be adapted in time and, hence, avoiding unpleasant abrupt changes. Hence, dynamic lighting effects (scripts) can be either speed-up/-down and, hence, they can be ramp-down/-up in areas of crowdedness or emptiness, respectively.
6. In addition, the knowledge of crowdedness is useful to reduce dynamics of effects and the interaction of individuals with the lighting system in such crowded areas, which would disturb the rest of the shoppers in the particular semantic area. This includes, that local light-stimulated focus (attention) points would be disable/enabled in areas with crowdedness or emptiness, respectively.
7. The identification or prediction of semantic areas exhibiting crowdedness or emptiness, respectively, can be used to adapt the environment stimuli (light effects, color dynamics, music, fragrance, temperature, humidity) striving to improve the well-being and the experience. For example, semantic areas with the attribute crowdedness will be appropriately steered with stress reducing ambiences and experiences, e.g. smooth light and music. On contrary, the environment stimuli in semantic areas exhibiting emptiness will be appropriately adapted, e.g. by providing guidance (e.g. guiding light) and increasing the dynamics of environmental stimuli to reduce the feeling of lowliness.
8. Last but not least, the knowledge of crowdedness or emptiness, respectively, of semantic areas can be used to exploit the emptiness of individual semantic areas to calibrate the lighting system during opening hours and, hence, reducing the costly shop downtime currently required installing and calibrating the light infrastructure.

At least some of the functionality of the invention may be performed by hard- or software. In case of an implementation in software, a single or multiple standard microprocessors or microcontrollers may be used to process a single or multiple algorithms implementing the invention.

It should be noted that the word "comprise" does not exclude other elements or steps, and that the word "a" or "an" does not exclude a plurality. Furthermore, any reference signs in the claims shall not be construed as limiting the scope of the invention.

The invention claimed is:

1. A system for automatically adjusting a lighting atmosphere based on presence detection, the system comprising
at least one sensor for gathering information associated with a presence level of people in a supervised area, said gathered information including the number of people in the supervised area and the number of people passing through the supervised area, and
a processing unit for determining the presence level of people in the supervised area based on the gathered information and for adjusting the lighting atmosphere based on the determined presence level by controlling the dynamics level and interactivity level of the lighting atmosphere depending on the determined presence level,
wherein the processing unit is configured:
to compare the determined presence level with a threshold and to adjust the lighting atmosphere, if the determined presence level is above the threshold, and
to control said dynamics level and said interactivity level of the lighting atmosphere such that one or more dynamic effects of the lighting atmosphere are either disabled or visibly altered, if the determined presence level is above the threshold.

2. The system of claim 1, wherein the at least one sensor is selected from the group consisting of: a grid of infra-red presence sensors; a floor embedded presence sensor; and a computer vision camera.

3. The system of claim 1, wherein the processing unit is further configured to receive the gathered information from the at least one sensor wirelessly.

4. The system of claim 1, wherein the processing unit is further adapted for adjusting the lighting atmosphere based on the determined presence level by controlling the dynamics level of the lighting atmosphere directly depending on the determined presence level, wherein the level of dynamics is lowered if the determined presence level raises.

5. The system of claim 4, wherein the processing unit is further adapted for setting the level of dynamics to the lowest level, if the determined presence level is above a threshold.

6. An atmosphere creation system comprising
a lighting system comprising at least one light unit and being adapted to automatically generate a lighting atmosphere with the at least one light unit,
a presence sensor electronically connected to a processing unit, said presence sensor capable of detecting the number of people in a supervised area and the number of people passing through said supervised area;
said processing unit operable to determine a presence level in said supervised area;
a system for automatically adjusting the generated lighting atmosphere based on said present level by controlling the lighting system including control of a dynamics level and an interactivity level of said lighting system such that one or more dynamic effects of said lighting system and said interactivity level are disabled when said presence level is above a predetermined threshold.

7. Method for automatically adjusting a lighting atmosphere based on presence detection, comprising
gathering information on a presence level of people in a supervised area by detecting the number of people in said supervised area and detecting the number of people passing through said supervised area,
determining the presence level of people on the supervised area based on the gathered information, and
adjusting the lighting atmosphere based on the determined presence level by controlling the dynamics level and the interactivity level of the lighting atmosphere depending on the determined presence level;
disabling said interactivity level of said lighting atmosphere when said determined presence level is determined to be above a predetermined threshold, said predetermined threshold representative of a high level of occupation of people in said supervised area.

* * * * *